(12) United States Patent
Polson et al.

(10) Patent No.: US 10,433,548 B2
(45) Date of Patent: Oct. 8, 2019

(54) BIOCIDAL COMPOSITIONS COMPRISING IRON CHELATORS

(71) Applicant: Arch Chemicals, Inc., Atlanta, GA (US)

(72) Inventors: George Polson, Jasper, GA (US); Jody Jourden, Atlanta, GA (US); Qi Zheng, Cumming, GA (US); Regina M. Prioli, Alpharetta, GA (US); Diana Ciccognani, Cumming, GA (US); Sungmee Choi, Alpharetta, GA (US)

(73) Assignee: Arch Chemicals, Inc., Morristown, NJ (US)

( * ) Notice: Subject to any disclaimer, the term of this patent is extended or adjusted under 35 U.S.C. 154(b) by 0 days.

(21) Appl. No.: 14/053,498

(22) Filed: Oct. 14, 2013

(65) Prior Publication Data

US 2014/0154189 A1    Jun. 5, 2014

Related U.S. Application Data

(60) Provisional application No. 61/713,283, filed on Oct. 12, 2012.

(51) Int. Cl.
*A01N 55/02* (2006.01)
*A01N 37/16* (2006.01)
(Continued)

(52) U.S. Cl.
CPC ............. *A01N 37/40* (2013.01); *A01N 43/40* (2013.01); *A01N 43/653* (2013.01); *A01N 43/80* (2013.01);
(Continued)

(58) Field of Classification Search
CPC ..................................................... A01N 55/02
See application file for complete search history.

(56) References Cited

U.S. PATENT DOCUMENTS

| 2,786,847 A | 3/1957 | Cislak |
| 2,809,971 A | 10/1957 | Bernstein et al. |

(Continued)

FOREIGN PATENT DOCUMENTS

| JP | H09-278611 | 10/1997 |
| JP | 2002020207 | 1/2002 |

(Continued)

OTHER PUBLICATIONS

Pubchem. Retrieved Mar. 11, 2015. http://pubchem.ncbi.nlm.nih.gov/compound/2-Pyridinol-1-oxide#section=Top.*

(Continued)

*Primary Examiner* — Adam C Milligan
*Assistant Examiner* — Sarah Alawadi
(74) *Attorney, Agent, or Firm* — Dority & Manning, P.A.

(57) ABSTRACT

The present invention, therefore, is directed to an antimicrobial compositions that decreases the bioavailability of iron by introducing a higher-affinity iron-selective chelating agent capable of competing with microbial siderophores. In one aspect, the present invention relates to an antimicrobial composition including a potentiating antimicrobial composition including one or more antimicrobial agents and a chelator having a weight ratio of the antimicrobial agent to the chelator from about 1:1000 to about 1000:1.

19 Claims, 1 Drawing Sheet

(51) Int. Cl.

| | | |
|---|---|---|
| *A01N 37/40* | (2006.01) | |
| *A01N 43/40* | (2006.01) | |
| *A01N 43/653* | (2006.01) | |
| *A01N 43/80* | (2006.01) | |
| *A01N 59/16* | (2006.01) | |
| *A61K 8/27* | (2006.01) | |
| *A61K 8/42* | (2006.01) | |
| *A61K 8/44* | (2006.01) | |
| *A61K 8/49* | (2006.01) | |
| *A61Q 17/00* | (2006.01) | |
| *A61Q 19/00* | (2006.01) | |

(52) U.S. Cl.
CPC ............... *A01N 59/16* (2013.01); *A61K 8/27* (2013.01); *A61K 8/42* (2013.01); *A61K 8/44* (2013.01); *A61K 8/49* (2013.01); *A61K 8/4933* (2013.01); *A61Q 17/005* (2013.01); *A61Q 19/00* (2013.01); *A61K 2800/10* (2013.01); *A61K 2800/51* (2013.01); *A61K 2800/524* (2013.01); *A61K 2800/58* (2013.01)

(56) References Cited

U.S. PATENT DOCUMENTS

| | | | |
|---|---|---|---|
| 3,589,999 A | 6/1971 | McRae et al. | |
| 3,590,035 A | 6/1971 | Damico | |
| 3,773,770 A | 11/1973 | Damico | |
| 4,301,162 A | 11/1981 | Hasegawa et al. | |
| 4,818,436 A | 4/1989 | French et al. | |
| 4,935,061 A | 6/1990 | French et al. | |
| 4,957,658 A | 9/1990 | French et al. | |
| 5,160,527 A | 11/1992 | Law et al. | |
| 5,562,995 A | 10/1996 | Kappock et al. | |
| 5,883,154 A | 3/1999 | Kappock et al. | |
| 5,939,203 A | 8/1999 | Kappock et al. | |
| 6,096,122 A | 8/2000 | Kappock et al. | |
| 2004/0143011 A1 | 7/2004 | Lutz et al. | |
| 2005/0129929 A1 | 6/2005 | Patton et al. | |
| 2005/0276862 A1 | 12/2005 | Bringley et al. | |
| 2008/0280792 A1 | 11/2008 | Williams | |
| 2011/0111245 A1 | 5/2011 | Warburton et al. | |
| 2012/0015986 A1 | 1/2012 | Hall et al. | |
| 2012/0219610 A1 | 8/2012 | Smith et al. | |
| 2012/0220516 A1 | 8/2012 | Smith et al. | |
| 2013/0109664 A1 | 5/2013 | Schwartz et al. | |

FOREIGN PATENT DOCUMENTS

| | | | |
|---|---|---|---|
| JP | 2007-008851 | | 1/2007 |
| WO | WO 2011/056667 | | 5/2011 |
| WO | WO2012/058557 | * | 5/2012 |
| WO | WO 2012/167368 | | 12/2012 |

OTHER PUBLICATIONS

Search Report and Written Opinion for PCT/US2013/064851 dated Jun. 12, 2013.
Robinson, M. A. Journal of Inorganic and Nuclear Chemistry (1964), 26(7), 1277-81. (Abstract).
U.S. Appl. No. 13/954,285, filed Jul. 30, 2013.
Search Report and Written Opinion for PCT/US2013/052688, dated Oct. 11, 2013

* cited by examiner

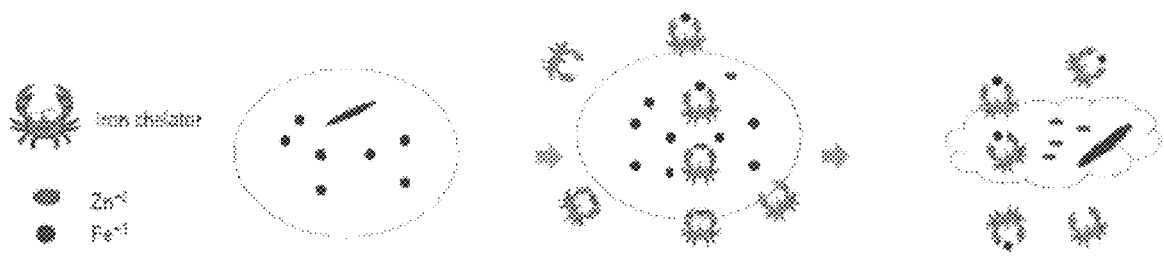

BIOCIDAL COMPOSITIONS COMPRISING IRON CHELATORS

RELATED APPLICATIONS

This application claims filing benefit of U.S. Provisional Patent Application Ser. No. 61/713,283, filed on Oct. 12, 2012, and which is incorporated herein by reference in its entirety

FIELD OF THE INVENTION

The present invention relates generally to antimicrobial compositions for use in preventing or mitigating mold, mildew, bacterial or algal contamination. In particular, the present invention relates to antimicrobial compositions comprising iron chelators that enhance the activity of antimicrobial agents in the composition.

BACKGROUND OF THE INVENTION

Mold, mildew and bacterial contamination are undesirable in consumer goods and on many types of surfaces. Control of such biological contamination has largely been based on the use of biocides. The use of synthetic or natural biocides or derivatives thereof efficiently and in an environmentally acceptable manner is becoming increasingly desirable and necessary.

Metal-ions such as silver, copper and gold ions have been found to possess antimicrobial properties, and compositions including these metal-ions have been used to prevent or inhibit the growth of microorganisms. Metal-ions, metal salts or compositions including these metal ions have been used to prevent the transmetal-ion sequestration of infectious disease and to kill harmful bacteria such as *Staphylococcus aureus* and *Salmonella* spp. While metals can be toxic to the microorganisms, they have been found to have an important role in various biological processes at lower concentrations. For example, metal-ions play a crucial role in oxygen transport in living systems, regulate the function of genes and replication in many cellular systems, and are involved in metabolism and enzymatic processes. As a result, the bioavailability of metal-ions in aerobic environments is a major factor in determining the abundance, growth-rate and health of plant, animal and microorganism populations.

Iron is an essential trace element for virtually all living organisms, because iron is an essential component for the proper functioning of many cellular enzymes and proteins. Although iron is one of the most abundant elements in the Earth's crust, it is not readily available for use by living organisms. The bioavailability of iron is limited because compounds of Fe(III), which is the most stable form of iron in air, are insoluble in aerobic environments. As a result, microorganisms use specialized iron uptake mechanisms to obtain this essential element. One such mechanism involves the production of siderophores, such as hydroxamates, catechols or carboxylates, which form water soluble complexes of Fe(III). These Fe(III)-siderophore complexes are then reduced to Fe(II) inside the microorganisms to release the iron for metabolic functions within the microorganisms. Thus, decreasing the bioavailability of iron from an aerobic environment may inhibit the growth of such microorganisms. Several siderophore-antibiotic conjugates have been developed to be used as antibacterial agents. These conjugates compete with the siderophores by selectively chelating with the iron, thereby depriving the microorganism of iron essential for its growth and metabolic activity. However, these conjugates have not been efficient and have not produced promising results in controlling or eradicating microbial contaminations.

Accordingly, there remains a very real and substantial need for antimicrobial compositions capable of effectively controlling and/or inhibiting microbial growth in industrial aqueous systems and in articles of manufacture. Because of increasing environmental regulations, there is still a further need to provide biocidal compositions having enhanced antimicrobial effect which are effective in lower doses than historically used. Use of lower amounts of biocides has a favorable impact on the environment, and allows users to realize significant cost savings. The present invention seeks to fulfill these needs and provides further related advantages.

SUMMARY OF THE INVENTION

The present invention, therefore, is directed to antimicrobial compositions that decrease the bioavailability of iron by introducing a higher-affinity iron-selective chelating agent capable of competing with microbial siderophores. Because the iron chelator will compete with the siderophores and selectively form a complex with the iron, they will starve microorganisms of an essential nutrient to stress the microorganism. Stressed microorganisms will become vulnerable to antimicrobial actives in the composition, thereby enhancing the activity of the antimicrobial composition. In one aspect, the present invention relates to antimicrobial compositions including effective amounts of iron-chelator and an antimicrobial agent. These and other aspects will become apparent upon reading the following detailed description of the present invention.

BRIEF DESCRIPTION OF THE DRAWINGS

FIG. 1 illustrates an exemplary mechanism by which chelators are able to permeabilize into a microbial cell and selectively capture iron from the microbial cell.

DETAILED DESCRIPTION OF THE INVENTION

The present invention is directed to an antimicrobial composition that decreases the bioavailability of iron by introducing a high-affinity iron-selective chelating agent capable of competing with microbial siderophores.

As used herein, the terms "chelator" and "chelating agent" refer to a molecule comprising nonmetal atoms, two or more of which atoms are capable of linking or binding with a metal ion to form a heterocyclic ring including the metal ion.

As used herein, the terms "antimicrobial," "biocide," and "inhibiting microbial growth" refer to the killing of, the inhibition of, or the control of the growth of bacteria, yeast, mold, and/or algae.

As used herein, the term "potentiate" means to enhance or increase at least one biological effect or activity of a biologically and/or pharmacologically active agent so that either (i) a given concentration or amount of the agent results in a greater biological effect or activity when the agent is potentiated than the biological effect or activity that would result from the same concentration or amount of the agent when not potentiated; or (ii) a lower concentration or amount of the agent is required to achieve a particular biological effect or activity when the agent is potentiated than when the agent is not potentiated; or (iii) both (i) and (ii). The biological effect or activity may be, for example, the ability to catalyze or inhibit one or more chemical reactions, the ability to activate or inhibit a biological or biochemical pathway, the ability to reduce or inhibit microbial proliferation, the ability to kill a microorganism, etc. An agent whose presence potentiates another agent may be referred to as a "potentiating agent." A potentiating agent may show biological activity by itself, or may exhibit biological activity only when used in combination with a biologically and/or pharmacologically active agent One aspect of the present invention is directed to an antimicrobial composition including one or more antimicrobial agents and a metal-ion chelator. The antimicrobial agent(s) can be selected after determining the composition and antibiotic resistance spectrum of the invading microbial population. The chelating agent will have a potentiating effect on the ability of the composition to inhibit the growth of microorganisms. In particular, the chelating agent will potentiate the activity of the antimicrobial agent, thereby reducing bioavailable concentration of metal ions to a level below a threshold level needed to support microorganism survival. The role of metal ions in biological processes within microbial species are generally numerous and include processes of nutrition and reproduction such as DNA replication, cell division, protein synthesis, RNA synthesis. Exemplary metal ions required by various biological processes within the microorganisms include $Zn^{2+}$, $Mg^{2+}$, $Mn^{2+}$, $Co^{2+}$, $Fe^{2+}$, and the like.

A particularly important feature of the antimicrobial composition of the present invention is their ability to decrease the bioavailability of iron by introducing a high-affinity iron-selective chelating agent capable of competing with microbial siderophores. While not intending to be bound by any particular theory of action, this ability to decrease the bioavailability of iron is believed to be the result of the iron chelator competing with the siderophores and selectively forming a complex with the iron, thereby starving microorganisms of an essential nutrient and stressing the microorganism. Stressed microorganisms will become vulnerable to antimicrobial actives in the composition, thereby potentiating the activity of the antimicrobial composition. FIG. 1 graphically illustrates an exemplary mechanism by which lipophilic Zn-chelators are able to permeabilize into a microbial cell, exchange $Zn^{2+}$ with $Fe^{3+}$, and take the chelated $Fe^{3+}$ out of the cell.

Metal-ion chelators may be selected from organic molecules capable of forming complexes with metal-ions. In some embodiments of the present invention, the metal-ion chelators include organic functional groups known to be strong "chelators" or sequestrants of metal-ions. Exemplary functional groups that are chelators or sequestrants of metal-ions include alpha-amino carboxylates, hydroxamates, catechols, pyridinones, hydroxyquinolines and the like. Alpha-amino carboxylates have the general formula:

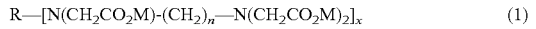

where R is an organic group such as an alkyl or aryl group; M is H, or an alkali or alkaline earth metal such as Na, K, Ca or Mg, or Zn; n is an integer from 1 to 6; and x is an integer from 1 to 3. Exemplary metal-ion chelators containing alpha-amino carboxylate functional groups include ethylenediaminetetraacetic acid (EDTA), diethylenetriaminepentaacetic acid (DTPA), hydroxylpropylenediaminetetraacetic acid (DPTA), ethylenebis-N,N'-(2-o-hydroxyphenyl)glycine (EHPG), 1,3-diaminopropane-N,N,N',N'-tetraacetic acid (PDTA), ethylenediamine-N,N'-diacetic acid (EDDA), ethylenediamine-N,N'-dipropionic acid dihydrochloride (EDDP), ethylenediamine-N,N'-bis(methylenephosphonic acid), N-(2-hydroxyethyl)ethylenediamine-N,N',N'-triacetic acid (HEDTA), ethylenediamine-N,N,N',N'-tetrakis(methylenephosponic acid) (EDTPO), O,O'-bis(2-aminoethyl)ethyleneglycol-N,N,N',N'-tetraacetic acid (EGTA); N,N-bis(2-hydroxybenzyl)ethylenediamine-N,N-diacetic acid (HBED), 1,6-hexamethylenediamine-N,N,N',N'-tetraacetic acid; N-(2-hydroxyethyl)iminodiacetic acid (HEIDA), iminodiacetic acid (IDA), 1,2-diaminopropane-N,N,N',N'-tetraacetic acid (Methyl-EDTA), nitrilotriacetic acid (NTA), nitrilotripropionic acid, nitrilotris(methylenephosphonic acid), triethylenetetramine-N,N,N',N'',N''',N'''-hexaacetic acid (TTHA), and the like.

Hydroxamates (or often called hydroxamic acids) have the general formula:

$$R—(CO)—N(OH)—R \quad (2)$$

where R is an organic group such as an alkyl or aryl group. Examples of metal-ion chelators containing hydroxamate functional groups include acetohydroxamic acid, salicylhydroxamic acid, and the iron chelating drug desferal (desferrioxamine) and the like.

Catechols have the general formula:

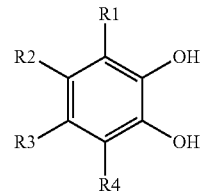

where R1, R2, R3 and R4 may be H, an organic group such as an alkyl or aryl group, or a carboxylate or sulfonate group. Examples of metal-ion sequestrants containing catechol functional groups include catechol, disulfocatechol, dimethyl-2,3-dihydroxybenzamide, mesitylene catecholamide (MECAM) and derivatives thereof, 1,8-dihydroxynaphthalene-3-,6-sulfonic acid, and 2,3-dihydroxynaphthalene-6-sulfonic acid.

Pyridinones are hetero-aryl compounds having at least one nitrogen in the ring structure and at least one hydroxyl substituent disposed on the ring structure so as to provide together, a chelating function. They have the general formula:

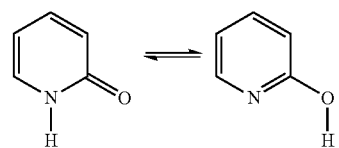

Examples of exemplary pyridinone chelants include 2-pyridinone, 2-hydroxypyridine-N-oxide (2-HPNO), 2,3-dihydroxypyridone, 2,4-dihydroxypyridone, 2,5-dihydroxypyridone, 2,6-dihydroxypyridone, 2,3-dihydroxypyridine, 2,4-dihyroxypyridine, 2,5-dihydroxypyridine, 2,6-dihydroxypyridine, 2,4,6-trihydroxypyridine, 3-hydroxy-4-pyridone, 2-hydroxy-3-methylpyridine, 2-hydroxy-4-methylpyridine, 2-hydroxy-5-methylpyridine, 2-hydroxy-6-methylpyridine, 2,6-dihydroxy-4-methylpyridine, 2-hydroxy-3-aminopyridine, 2-hydroxy-4-aminopyridine, and the like, and any combination thereof.

Any 8-hydroxyquinolines may also be employed as a chelator in the compositions of the present invention. 8-hydroxyquinolines have the formula:

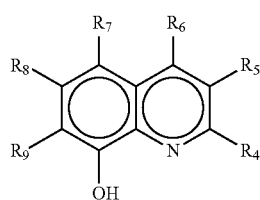

(5)

in which $R_4$ to $R_9$, which are identical or different, denote a hydrogen atom or hydrocarbon radicals containing from 1 to 20 and preferably from 1 to 12 carbon atoms, a halogen atom, an —$SO_3H$, —$NO_2$ or carboxy group. More preferably, $R_4$ to $R_9$ denote an alkyl radical containing from 1 to 20 carbon atoms, such as methyl, ethyl, n-propyl, isopropyl, n-butyl, isobutyl, n-pentyl, n-hexyl, n-heptyl, 2-ethylhexyl, octyl or decyl radicals; a cycloalkyl radical optionally substituted by 1 to 3 lower alkyl radicals, such as cyclopentyl, cyclohexyl, methylcyclohexyl or ethylcyclohexyl; an aryl radical optionally substituted by 1 to 3 lower alkyl radicals, such as phenyl, toluyl or xylyl radicals; an arylalkyl radical containing from 1 to 4 carbon atoms in the alkyl moiety, such as benzyl or B-phenylethyl radical; a halogen atom such as fluorine, chlorine or bromine; and a linear or branched alkenyl radical containing from 2 to 20 carbon atoms and one or more ethylenic double bonds, such as vinyl, 2-propenyl, 2-butenyl, isobutenyl, or 3,3,5,5,-tetramethyl-1-vinylhexyl. The sum of the carbon atoms in the various substituents $R_4$ to $R_9$ preferably does not exceed 20 and up to three of the radicals $R_4$ to $R_9$ may denote an —$SO_3H$, —$NO_2$ or —COOH group or a halogen atom. Representative examples of 8-hydroxyquinolines include 8-hydroxyquinoline, 2-methyl-8-hydroxyquinoline, 3-ethyl-8-hydroxyquinoline, 6-ethyl-8-hydroxyquinoline, 2-isopropyl-8-hydroxyquinoline, 7-n-pentyl-8-hydroxyquinoline, 2-cyclohexyl-8-hydroxyquinoline, 2-phenyl-8-hydroxyquinoline, 3-benzyl-8-hydroxyquinoline, 5,7-dichloro-2-methyl-8-hydroxyquinoline, 5-chloro-8-hydroxyquinoline, 5-chloro-2-methyl-8-hydroxyquinoline, 5,6,7-trichloro-8-hydroxyquinoline, 5,7-dibromo-8-hydroxyquinoline, 5,7-dibromo-2-methyl-8-hydroxyquinoline, 5-sulfonyl-8-hydroxyquinoline, 7-sulfonyl-8-hydroxyquinoline, 5-nitro-8-hydroxyquinoline, 2-methyl-5-nitro-8-hydroxyquinoline, 2-chloro-5-nitro-8-hydroxyquinoline, 5-carboxy-8-hydroxyquinoline and 2-(3,3,5,5-tetramethyl-1-vinylhexyl)-8-hydroxyquinoline, and the like.

In some embodiments of the present invention, chelators for use include, but are not limited to barium, bismuth, calcium, cobalt, copper, dysprosium, europium, indium, lanthanum, magnesium, manganese, nickel, samarium, silver, sodium, strontium, and zinc salts of the aforementioned chelates.

Antimicrobial agent(s) that may be included in the various embodiments of the compositions include, but are not limited to pyrithione salts; amines; salicylic acid; benzoyl peroxide; 2,2'-dithiobis(pyridine-1-oxide); 10,10'-oxybisphenoxarsine; N-(trichloromethylthio)-4-cyclo-hexene-1,2-dicarbonamide; 2,3,5,6-tetrachloro-4-(methlysulfonyl)pyridine; N-(trichloromethylthio)phthalimide; N-hydroxy-6-octyloxypyridine-2(1H) one ethanolamine salt; dodecylbis (hydroxyethyl)dioctyl ammonium phosphate, dodecylbis (hydroxyethyl) octyl hydrogen ammonium phosphate, and other phosphate amines; 3-trimethyoxysilylpropyl dimethyloctadecylammonium chloride and other quaternary ammonia compounds including quaternary ammonium salts; 2,4,4'-trichloro-2'-hydroxy-diphenylether and other phenol derivatives such as 2 phenylphenol or dichlorophene or 2,2'-methylenebis(4-chlorophenol); diodomethyl-p-tolyl sulfone, isothiazolinones such as 2-n-octyl-4-isothiazolin-3-one and other isothiazoline derivatives such as benzisothiazoline, butylbenzisothiazolinone, and their combinations; organometallics such as tributyltin compounds such as tributyltinoxide or tributyltin maleate; dithio-2,2'-bis(benzmethylamide); N-trichloromethylthio-4-cyclohexene-1,2-dicarboximide; 2-(4-thiazolyl)benzimidazole; thiocyanic acid; 2-benzothiazolylthio)methyl ester; 2,4,5,6, tetrachloro-1,3-benzenedicarbonitrile; 2[(trichloromethyl)thio]-1H-isoindole-1,3(2H)-dione; 3a,4,7,7a-tetrahydro-2[(trichloromethyl)thio]-1H-isoindole-1,3(2H)-dione; 1,1-dichloro-N-methanesulfamide; alkoxysiloxane quaternary compounds; copper-8-quinolinolate; copper napthenate; copper-2-ethylhexoate; parabens; carbamatates such as iodopropynyl butylcarbamate and the like; azoles such as propiconazole and the like; and sulfur compounds. Exemplary pyrithione salts used in the composition of the present invention include sodium pyrithione, zinc pyrithione, chitosan pyrithione, magnesium disulfide pyrithione, copper pyrithione, and the like. The antimicrobial agents may be used individually or in combination.

Another aspect of the present invention is directed to a potentiating antimicrobial composition including an antimicrobial agent and a chelator having a weight ratio of the antimicrobial agent to the chelator in a range from about 1:1000 to 1000:1. The present invention is further directed to a method for inhibiting microbial growth in an aqueous system or on an article of manufacture prone to such growth, which method comprises treating said system or said article with an effective amount of an antimicrobial combination of an antimicrobial agent and a chelator, wherein the weight ratio of the antimicrobial agent to the chelator ranges from about 1:1000 to 1000:1.

In accordance with the present invention, the weight ratio of the two components—antimicrobial agent and chelator—of the potentiating combination are dictated by the dosage levels of each component which demonstrate potentiation, based on 100% active ingredient, relative to each end use application. Typically, the weight ratio of an antimicrobial agent and a chelator ranges from about 1:1000 to about 1000:1 on an active basis, such as from about 1:500 to about 100:1, such as from about 1:100 to about 100:1, such as from about 1:100 to about 10:1, such as from about 1:10 to about 10:1, such as from about 1:10 to about 1:1 or such as from about 1:5 to about 5:1, such as from about 1:5 to about 1:1. As will be understood by one skilled in the art, however, the potentiating weight ratio of the two components generally varies to some extent depending on the application and the organism being controlled.

One embodiment of the present invention is directed to a potentiating antimicrobial composition including (a) one or more antimicrobial agents selected from zinc pyrithione (ZPT), benzisothiazolinone (BIT), butylbenzisothiazolinone (BBIT), iodopropynyl butylcarbamate (IPBC), propiconazole (PROP), salicylic acid, and benzoyl peroxide; and (b) a chelator selected from diethylenetriaminepentaacetic acid, N,N'-bis(o-hydroxybenzyl) ethylenediamine-N,N'diacetic acid, ethylenebis-N,N'-(2-o-hydroxyphenyl)glycine (EHPG), O,O'-bis(2-aminoethyl)ethyleneglycol-N,N,N',N'-tetraacetic acid (EGTA), 8-hydroxyquinoline (8-HQ), 2-hydroxypyridine-1-oxide (2-HPNO), 8-hydroxyquinoline zinc salt (8-HQ-Zn), salicylaldehyde isonicotinoyl hydrazone zinc salt (SIH-Zn), thenoyl trifluoro acetone zinc salt (Then-Zn), and 2-hydroxypyridine-1-oxide zinc salt (HPNO-Zn), zinc dihydroxyacetate (DHA-Zn), zinc(tropolone)$_2$ (Trop-Zn), hydroxyethylidene-1,1'-diphosphonic acid and its potassium or zinc salts, dehydroacetic acid (DHA) and glucoheptanoic acid or glucoheptanoic acid zinc salt (GlucHep-Zn). The weight ratio of the antimicrobial agent to the chelator is from about 1:1000 to about 1000:1 on an active basis, such as from about 1:500 to about 100:1, such as from about 1:100 to about 100:1, such as from about 1:100 to about 10:1, such as from about 1:10 to about 10:1, such as from about 1:5 to about 5:1, such as from about 1:5 to about 1:1.

An effective amount of a potentiating combination of an antimicrobial agent and a chelator may be added to an aqueous system being treated. At least 0.1 parts per million (ppm), based on the weight of water in the system being treated, of the potentiating combination described above is added. In one embodiment, between about 1 ppm and about 10000 ppm, such as from about 10 ppm to about 5000 ppm, such as from about 10 ppm to about 1000 ppm, such as from about 50 ppm to about 1,000 ppm, such as from about 50 ppm to about 500 ppm of an antimicrobial agent and between about 10 ppm and 2000 ppm, such as from about 10 ppm to about 1500 ppm, such as from about 10 ppm to about 1000 ppm, such as from about 50 ppm to about 500 ppm, such as from about 100 ppm to about 500 ppm of a chelator, based on the weight of water in the system being treated, can be added. It is well within the ordinary skill of one practicing in the art to determine the effective amount of biocide for a given system based on various system parameters including but not limited to the size of the system, pH of the system, the types of organisms present and the amount of control desired.

Likewise, an effective amount of a potentiating combination of an antimicrobial agent and a chelator can be applied to the article of manufacture being treated. Generally, a solution of the potentiating antimicrobial combination described above having a concentration of at least 0.1 ppm is incorporated into, sprayed onto, used to dip, or otherwise applied to the substrate being treated in order to prevent growth of bacteria, mold, yeast and algae. Again, it is well within the ordinary skill of one practicing in the art to determine the effective amount of biocide to apply to a given article of manufacture being treated.

The active ingredients of the potentiating antimicrobial compositions of the present invention may be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the potentiating antimicrobial combinations are liquid, they may be employed neat or may be incorporated into various formulations, both solid and liquid, as an adsorbate on suitable inert carriers such as talc, clays, diatomaceous earth and the like, or water and various organic liquids such as lower alkanols, kerosene, benzene, toluene, and other petroleum distillate fractions or mixtures thereof.

It will also be understood by one skilled in the art that the potentiating antimicrobial combination disclosed herein may be used in combination with other antimicrobial materials. For example, the combination can be combined with other fungicides and bactericides in appropriate concentrations and in appropriate instances so as to combine the action of each to obtain particularly useful results. Such combinations might find particular application in the preparation of germicidal soaps, in the production of cosmetics and aqueous coatings and in combating metal-working fluid slime accumulations. The potentiating antimicrobial combination of the present invention can be combined with other algicidal agents as well.

In accordance with the present invention there is still further provided a method of inhibiting the growth of at least one of: bacteria, yeast, mold and algae. According to the methods of the present invention, this growth is inhibited in aqueous systems or on articles or products of manufacture prone to such growth. These methods comprise adding to the aqueous system or treating the article or product containing said bacteria, yeast, mold and/or algae with an effective amount of a potentiating combination of an antimicrobial agent and a chelator. This addition can be accomplished either by simple addition of the antimicrobial agent and the chelator together as a single admixture, or by addition of the two components separately. Such separate administration can either be at the same time or at different times.

As noted above, the present invention is based upon the discovery that use of an antimicrobial agent in conjunction with a chelator produces potentiating results and is effective in controlling the growth of bacteria, yeast, mold and algae in a variety of industrial and other applications. The utility of the potentiating antimicrobial combination disclosed herein derives from its versatility both in the numerous industries in which it can be applied, as well as the numerous microorganisms against which it is effective.

For instance, the composition of the present invention may provide utility as a metal working fluid, for polymer preservation, for personal care formulations, and for material protection. The composition of the present invention may also provide utility in a water based coating, a water based paint, a water based ingredient for paint, pesticide formulations, adhesives, household cleaning products, aqueous dispersions, sealants and caulks, inks, and the like.

The superior antimicrobial activity of the potentiating antimicrobial combination of an antimicrobial agent and a chelator has been confirmed using standard laboratory techniques. The antimicrobial combination has been found effective, for example, in inhibiting microbial growth including but not limited to the bacteria *S. aureus*, *B. subtilis*, *S. epidermidis*, *E. hirae*, *E. coli*, *P. aeruginosa*, *C. albicans*, *M. furfur*, *S. cerevisie*, *A. brasiliensis*, *A. pullulans*, *T. mentagrophytes*, *C. pyrenoidosa*, *R. subcapitata*, *P. acnes*, and *P. faveolarum*. The combination is also believed to be effective against other microbial species including, but not limited to, *Aerobacter aerongenes*, *Aeromonas* spp., *Bacillus* spp., *Bordetella* spp, *Campylobacter* spp., *Chlamydia* spp., *Corynebacterium* spp., *Desulfovibrio* spp., enteropathogenic *E. coli*, Enterotoxin-producing *E. coli*, *Helicobacter pylori*, *Klebsiella pneumoniae*, *Legionella pneumophila*, *Leptospira* spp., *Mycobacterium tuberculosis*, *M. bovis*, *Neisseria gonorrhoeae*, *N. meningitidis*, *Nocardia* spp., *Proteus mirabilis*, *P vulgaris*, *Rhodococcus equi*, *Salmonella enteridis*, *S. typhimurium*, *S. typhosa*, *Shigella sonnei*, *S. dysenterae*, *Streptococcus anginosus*, *S. mutans*, *Vibrio cholerae*, *Yersinia pestis*, *Y. pseudotuberculosis*, *Actinomycetes* spp., and *Streptomyces* spp.

The potentiating antimicrobial composition disclosed in the present invention is also applicable to the control of bacterial and fungal growth in cosmetic and personal care products. Such products include but are not limited to creams, lotions, shampoos, conditioners, sunscreens, hand cleaners, acne control formulations, soaps, liquid hand soaps, detergents, hospital scrubs, bactericidal washes, deodorants, and the like. Cosmetic and personal care products subject to microbiological attack can suffer from separation of emulsions, discoloration, unsightly visible colonies, malodor, and change of pH; microbial growth in these products can also lead to potential health hazards.

Embodiments of the invention provide a safe and effective method of slowing bacterial growth on the skin. The invention also provides a safe and effective method of improving wound care products, antiperspirants and could be used in topical antimicrobial personal care products. The human skin is a complex organ providing many functions and serves as a primary barrier for preventing infections while at the same time playing host to many commensal microbial organisms. Microorganisms that can be regularly isolated from the skin include *Staphylococcus*, and *Corynebacterium, Micrococcus, Propionibacterium*, and *Trichophyton* and *Malassezia* yeasts. Other bacteria like *E. coli* and *P. aeruginosa* also colonize the human skin and are responsible for various human afflictions. While some iron chelators have been identified to reduce body malodor causing bacteria, others have been shown to enhance the efficacy of anti-dandruff actives as well as certain antibiotics.

EXAMPLES

A more complete understanding of the present invention can be obtained by referring to the following illustrative examples of the practice of the invention, which examples are not intended, however, to limit the invention.

Example 1

Efficacy of Antimicrobial Agents with and without Chelators Against Microorganisms In Vitro Activities of antimicrobial compositions of the present invention were tested against a range of typical skin microorganisms in a Minimum Inhibitory Concentration (MIC) test. MICs for the organisms were determined in a standard 96-well microtiter plate assay in Brain Heart Infusion Broth (BHI) for *P. acnes*; Tryptic Soy Broth (TSB) for the remaining bacteria; Ushijima Broth for *M. furfur*; Sabouraud Dextrose Broth (SDB) for other fungi. Samples were tested in duplicate on separate plates. For bacteria and fungi plates, samples were serially diluted into double strength media on the microtiter plates. The bacterial or fungal inocula, suspended in sterile deionized water, were then added to the wells in 1:1 ratio to the medium. The final concentration of bacteria in the wells was $5 \times 10^5$ CFUs/mL, the final concentration of fungi was $5 \times 10^4$ cells or spores/mL. Plates were incubated: anaerobically at 35° C. for 7 days for *P. acnes*; aerobically at 35° C. for 2 days for the remaining bacteria and aerobically at 35° C. for 7 days for *M. furfur*; aerobically at 28° C. for 7 days for *T. mentagrophytes*. Following incubation, the minimum concentration of active observed to completely inhibit growth (MIC) was visually determined.

Tables 1-5 show the minimum concentration of antimicrobial agents, with and without chelators, required for an inhibitory effect against a wide range of skin bacteria. When evaluating the potentiation effects of the iron chelators themselves by MIC, little potentiation of the antimicrobial actives is observed. However, when these iron chelators are present as their zinc complexes, an improvement in their ability to enhance the activity of the antimicrobials is seen. Table 6 highlights this theory with data for ZPT plus chelators and their Zn salts. The lipophilic nature of the zinc chelates endear them to be membrane permeable and once inside the cell, they are able to exchange iron for zinc thereby depriving the organism of essential Fe needed for metabolic functions. This deprivation of intercellular iron renders the micro-organisms more vulnerable to antimicrobials and hence provides an attractive strategy to enhance the efficacy of topical treatments. All chelators listed showed significant improvement of activity of salicylic acid and benzoyl peroxide against *P. acnes*. Table 7 shows MIC values (ppm) of salicylic acid and benzoyl peroxide with and without chelators tested against *P. acnes*.

TABLE 1

| Potentiator | Molar Eq (Pot:ZPT) | *B. subtilis* | *S. epidermidis* | *P. aeruginosa* | *C. albicans* | *M. furfur* | *A. brasiliensis* | *T. mentagrophytes* | *C. pyrenoidsa* | *R. subcapitata* | *P. faveolarum* |
|---|---|---|---|---|---|---|---|---|---|---|---|
| ZPT | | 1.95-4 | 1.95-7.8 | 31-62 | 7.81 | 0.98-4 | 7.81-15.6 | 3.91-8 | 0.24-4 | 1.95-4 | 0.05-2 |
| HBED-Zn | 10:1 | 1.95 | 3.91 | 15.63 | 3.91 | 0.98 | 7.81 | 1.46 | 0.98 | 0.49 | 0.24 |
| 2-HPNO-Zn | 10:1 | 1.46 | 1.46 | 15.63 | 1.95 | 1.95 | 15.63 | 1.95 | 0.49 | 0.49 | 0.24 |
| 8-HQ-Zn | 1:1 | 0.98 | 1.95 | 31.25 | 7.81 | 1.95 | 15.63 | 3.91 | 0.73 | 1.95 | 0.24 |
| DHA-Zn | 10:1 | 0.98 | 3.91 | 31.25 | 3.91 | 1.95 | 7.81 | 0.49 | 0.98 | 0.98 | 0.05 |
| Tropolone-Zn | 10:1 | 0.24 | 0.18 | 15.63 | 0.73 | 0.73 | 1.95 | 0.18 | 0.98 | 0.49 | 0.05 |

TABLE 2

| Potentiator | Molar Eq (Pot:BIT) | *B. subtilis* | *P. aeruginosa* | *A. brasiliensis* | *A. pullulans* | *C. pyrenoidsa* | *R. subcapitata* | *P. faveolarum* |
|---|---|---|---|---|---|---|---|---|
| BIT | | 1.02-4 | 32.50 | 16-32.5 | 4.06-8 | 4.06-8 | 8.13 | 4.06-16 |
| DTPA | 10:1 | 2.03 | 8.13 | 16.25 | 2.03 | 0.51 | 0.51 | <0.06 |
| HBED | 10:1 | 0.51 | 8.13 | 32.50 | 4.06 | 2.03 | 4.06 | 4.06 |
| 2-HPNO-Zn | 10:1 | 1.02 | 16.25 | 24.38 | 8.13 | 1.52 | 2.03 | 0.38 |
| Tropolone-Zn | 10:1 | 0.13 | 8.13 | 1.02 | 0.24 | 0.76 | 1.02 | 0.19 |
| DHA-Zn | 10:1 | 1.52 | 32.50 | 6.09 | 2.03 | 2.03 | 2.03 | 0.25 |
| Then-Zn | 10:1 | 1.52 | 32.50 | 32.50 | 4.06 | 2.03 | 1.02 | 0.13 |

TABLE 3

| Potentiator | Molar Eq (Pot:BBIT) | B. subtilis | P. aeruginosa | A. brasiliensis | A. pullulans | C. pyrenoidsa | R. subcapitata | P. faveolarum |
|---|---|---|---|---|---|---|---|---|
| BBIT | | 1.88-2.5 | 80.00 | 1.25-5 | 2.5-5 | 1.25-2.5 | 1.25-15 | 1.25-5 |
| DTPA | 10:1 | 2.50 | 20.00 | 1.25 | 0.63 | 1.25 | 0.94 | 0.16 |
| 2-HPNO-Zn | 10:1 | 1.25 | 40.00 | 2.50 | 3.75 | 0.94 | 5.00 | 0.23 |
| Tropolone-Zn | 10:1 | 0.31 | 20.00 | 0.94 | 0.31 | 1.25 | 0.94 | 0.23 |
| Gluco-heptanoate-Zn | 10:1 | 1.25 | 80.00 | 2.50 | 5.00 | 1.25 | 1.88 | 0.16 |

TABLE 4

| Potentiator | Molar Eq (Pot:PROP) | S. aureus | B. subtilis | E. hirae | P. aeruginosa | C. albicans | C. pyrenoidsa | R. subcapitata | P. faveolarum |
|---|---|---|---|---|---|---|---|---|---|
| Propiconazole | | 82.5-165.00 | 82.50->165.00 | 165.00 | 165.00 | 41.25-100.00 | 20.63-82.5 | 20.63-41.25 | 20.63-41.25 |
| DHA-Zn | 10:1 | 41.25 | 30.94 | 20.63 | 165.00 | 0.64 | 10.31 | 1.29 | 1.93 |
| Tropolone-Zn | 10:1 | 0.64 | 0.64 | 0.32 | 41.25 | 0.97 | 2.58 | 1.29 | 0.32 |
| Gluco-heptanoate-Zn | 10:1 | 41.25 | 20.63 | 20.63 | 165.00 | 82.50 | 15.47 | 0.97 | 1.93 |

TABLE 5

| Potentiator | Molar Eq (Pot:IPBC) | S. aureus | B. subtilis | E. hirae | P. aeruginosa | C. albicans | C. pyrenoidsa | R. subcapitata | P. faveolarum |
|---|---|---|---|---|---|---|---|---|---|
| IPBC | | 16.25-31.50 | 32.5-63.00 | 32.5->63.00 | 65.00 | 1.02-2.03 | 0.38-1.97 | 1.52-7.88 | 2.03-7.88 |
| Then-Zn | 10:1 | 13.25 | 4.06 | 8.13 | 65.0 | 2.03 | 0.38 | 1.02 | 0.51 |
| 2-HPNO-Zn | 10:1 | 6.09 | 6.09 | 2.03 | 65.0 | 2.03 | 0.51 | 1.52 | 0.51 |
| Tropolone-Zn | 10:1 | 0.51 | 0.51 | 0.25 | 32.5 | 1.02 | 0.51 | 0.51 | 0.38 |

TABLE 6

| Active | Chelator | Molar Ratio | S. epidermidis | T. mentagrophytes | M. furfur | E. Coli | P. aeruginosa |
|---|---|---|---|---|---|---|---|
| ZPT | — | — | 1.95-7.8 | 3.91-5 | 1.25-1.95 | 1.95-7.81 | 31.25-62.5 |
| | HBED + Zn(II) | 10× | 0.98 | 0.49 | 3.91 | 15.63 | 62.5 |
| | | | 3.91 | 1.46 | 0.98 | 3.91 | 15.63 |
| | 8-HQ + Zn(II) | 5× | 0.49 | 7.81 | 1.95 | 7.81 | 125 |
| | | 1× | 1.95 | 3.91 | 1.95 | 7.81 | 31.5 |
| | 2-HPNO + Zn(II) | 10× | 7.8 | 1.95 | 1.95 | 7.8 | 31.25 |
| | | | 1.46 | 1.95 | 1.95 | 7.81 | 15.63 |

TABLE 7

| MIC values against P. acnes | | | |
|---|---|---|---|
| | | Salicylic Acid 100 ppm | Benzoyl Peroxide 200 ppm |
| Chelator | Molar Eq. | | |
| HBED | 10× | 3.13 | 3.13 |
| 8-HQ | 5× | 0.78 | 0.78 |
| DTPA | 10× | 3.13 | 6.25 |
| Desferrioxamine | 1× | 25 | 25 |

Example 2

Microbial Reduction Experiments

Time-kill test were performed to assess microbial reduction by antimicrobial agents, with and without chelators, against S. aureus, P. aeruginosa, and E. coli. Antimicrobial agents and/or chelators used for the test include zinc pyrithione (ZPT), 2-HPNO, 8-HQ, HBED, ZPT/2-HPNO, ZPT/8-HQ, and ZPT/HBED.

100 μL of sample and 100 μL of bacterial suspension at 5×10$^5$ cells/mL was loaded into the first well of each row in a 96-well plate, mixed and after specific contact time, 10-fold serial dilutions were made using a multichannel pipette by transferring 20 μL into 180 μL of Letheen broth, mixing 10 times. The process was repeated. Thereafter, three replicates of 10 μL from each of the six selected dilutions were plated onto Tryptic Soy Agar using a 2-20 μL monochannel pipette. Plates were allowed to dry, then placed into an incubator at 35° C. for 24 hrs. Colonies (0.5-1 mm) were enumerated using a colony counter. Tables 8-10 show log reductions (CFUs/mL) from an initial microbial population.

Evaluation of the iron chelators in combination with ZPT in time-kill studies showed significant reduction in CFUs when compared to ZPT and the chelator itself. HBED was found to be the best chelator.

TABLE 8

| | S. aureus | | | | E. coli | | | |
|---|---|---|---|---|---|---|---|---|
| | 4 hr | | 8 hr | | 4 hr | | 8 hr | |
| | CFU | log reduction | CFU | log reduction | CFU | log reduction | CFU | log reduction |
| Inoculum | $7 \times 10^6$ | | $>10^7$ | | $>10^7$ | | $3 \times 10^8$ | |
| ZPT | $9.3 \times 10^5$ | 1 | $1.2 \times 10^5$ | 2 | $>10^7$ | 0 | $>10^7$ | 0 |
| 2-HPNO | $1.6 \times 10^5$ | 1 | $2.3 \times 10^5$ | 2 | $3 \times 10^5$ | 2 | $3.6 \times 10^5$ | 3 |
| ZPT + 2-HPNO | $1.1 \times 10^4$ | 2 | $<10^3$ | 5 | $1.1 \times 10^4$ | 3 | $3.3 \times 10^3$ | 5 |

| | P. aeruginosa | | | |
|---|---|---|---|---|
| | 4 hr | | 8 hr | |
| | CFU | log reduction | CFU | log reduction |
| Inoculum | $>10^7$ | | $1.1 \times 10^8$ | |
| ZPT | $7.3 \times 10^6$ | 1 | $6.3 \times 10^6$ | 2 |
| 2-HPNO | $2.6 \times 10^5$ | 2 | $1.4 \times 10^6$ | 2 |
| ZPT + 2-HPNO | $<10^2$ | 5 | $<10^2$ | 6 |

TABLE 9

| | S. aureus | | | | E. coli | | | |
|---|---|---|---|---|---|---|---|---|
| | 4 hr | | 8 hr | | 4 hr | | 8 hr | |
| | CFU | log reduction | CFU | log reduction | CFU | log reduction | CFU | log reduction |
| Inoculum | $7 \times 10^6$ | | $>10^7$ | | $>10^7$ | | $3 \times 10^8$ | |
| ZPT | $9.3 \times 10^5$ | 1 | $1.2 \times 10^5$ | 2 | $>10^7$ | 0 | $>10^7$ | 0 |
| 8-HQ | $1.6 \times 10^5$ | 1 | $6.3 \times 10^5$ | 2 | $8.6 \times 10^5$ | 2 | $1.2 \times 10^6$ | 2 |
| ZPT + 8-HQ | $1.6 \times 10^4$ | 2 | $<10^2$ | 5 | $<10^2$ | 5 | $<10^2$ | 6 |

| | P. aeruginosa | | | |
|---|---|---|---|---|
| | 4 hr | | 8 hr | |
| | CFU | log reduction | CFU | log reduction |
| Inoculum | $>10^7$ | | $1.1 \times 10^8$ | |
| ZPT | $7.3 \times 10^6$ | 1 | $6.3 \times 10^6$ | 2 |
| 8-HQ | $2.6 \times 10^6$ | 1 | $3 \times 10^5$ | 3 |
| ZPT + 8-HQ | $<10^2$ | 5 | $<10^2$ | 6 |

TABLE 10

| | S. aureus | | | | E. coli | | | |
|---|---|---|---|---|---|---|---|---|
| | 4 hr | | 8 hr | | 4 hr | | 8 hr | |
| | CFU | log reduction | CFU | log reduction | CFU | log reduction | CFU | log reduction |
| Inoculum | $1.8 \times 10^7$ | | $>10^7$ | | $>10^7$ | | $3 \times 10^8$ | |
| ZPT | $1.1 \times 10^6$ | 1 | $2.6 \times 10^5$ | 2 | $>10^7$ | 0 | $>10^7$ | 0 |
| HBED | $1.4 \times 10^6$ | 1 | $2.3 \times 10^5$ | 2 | $8.3 \times 10^5$ | 2 | $1.6 \times 10^6$ | 2 |
| ZPT + 8-HQ | $<10^2$ | 5 | $<10^2$ | 5 | $<10^2$ | 5 | $<10^2$ | 6 |

TABLE 10-continued

| | | P. aeruginosa | | |
| --- | --- | --- | --- | --- |
| | | 4 hr | | 8 hr |
| | CFU | log reduction | CFU | log reduction |
| Inoculum | >$10^7$ | | $1.1 \times 10^8$ | |
| ZPT | $7.3 \times 10^6$ | 1 | $6.3 \times 10^6$ | 2 |
| HBED | >$10^7$ | 0 | $1.6 \times 10^5$ | 3 |
| ZPT + 8-HQ | <$10^2$ | 5 | <$10^2$ | 6 |

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. An antimicrobial composition comprising:
   a) at least one antimicrobial agent comprising a zinc pyrithione; and
   b) an iron-chelator comprising 2-hydroxypyridine-1-oxide or a salt thereof, 8-hydroxyquinoline or a salt thereof, or N,N-bis(2-hydroxybenzyl)ethylenediamine-N,N-diacetic acid or a salt thereof;
   wherein the at least one antimicrobial agent comprising a zinc pyrithione and 2-hydroxypyridine-1-oxide or a salt thereof are present in a weight ratio of the at least one antimicrobial agent comprising a zinc pyrithione to 2-hydroxypyridine-1-oxide or salt thereof of from 1:10 to 5:1, or the at least one antimicrobial agent comprising a zinc pyrithione and 8-hydroxyquinoline or a salt thereof are present in a weight ratio of the at least one antimicrobial agent comprising a zinc pyrithione to 8-hydroxyquinoline or a salt thereof of from 1:5 to 5:1, or the at least one antimicrobial agent comprising a zinc pyrithione and N,N-bis(2-hydroxybenzyl)ethylenediamine-N,N-diacetic acid or a salt thereof are present in a weight ratio of the at least one antimicrobial agent comprising a zinc pyrithione to N,N-bis(2-hydroxybenzyl)ethylenediamine-N,N-diacetic acid or a salt of from 1:100 to 1:10.

2. The antimicrobial composition of claim 1, wherein the iron-chelator comprises 2-hydroxypyridine-1-oxide.

3. The antimicrobial composition of claim 1, wherein the iron-chelator comprises a sodium, potassium, calcium, magnesium, or copper salt of 2-hydroxypyridine-1-oxide.

4. The antimicrobial composition of claim 1, wherein the iron-chelator comprises a zinc salt of 2-hydroxypyridine-1-oxide.

5. The antimicrobial composition of claim 1, wherein the composition is present in water and the at least one antimicrobial agent is present in an amount of from about 1 ppm to about 10,000 ppm and wherein the iron chelator is present in an amount of from about 10 ppm to about 2,000 ppm, based on the weight of the water.

6. A personal care composition comprising the antimicrobial composition of claim 1, the personal care composition selected from the group consisting of a cream, an ointment, a lotion, a shampoo, a conditioner, a sunscreen, a deodorant, a soap, a hand cleaner, a detergent, a scrub, a bactericidal wash, and an acne formulation.

7. A method of inhibiting microbial growth on a surface which comprises applying to said surface an effective amount of an antimicrobial composition comprising:
   a) at least one antimicrobial agent comprising a zinc pyrithione; and
   b) an iron-chelator comprising 2-hydroxypyridine-1-oxide or a salt thereof, 8-hydroxyquinoline or a salt thereof, or N,N-bis(2-hydroxybenzyl)ethylenediamine-N,N-diacetic acid or a salt thereof;
   wherein the composition is present in water and the at least one antimicrobial agent is present in an amount of from about 1 ppm to about 10,000 ppm and wherein the chelator is present in an amount of from about 10 ppm to about 2000 ppm, based on the weight of the water, and
   wherein the at least one antimicrobial agent comprising a zinc pyrithione and 2-hydroxypyridine-1-oxide or a salt thereof are present in a weight ratio of the at least one antimicrobial agent comprising a zinc pyrithione to 2-hydroxypyridine-1-oxide or salt thereof of from 1:10 to 5:1, or the at least one antimicrobial agent comprising a zinc pyrithione and 8-hydroxyquinoline or a salt thereof are present in a weight ratio of the at least one antimicrobial agent comprising a zinc pyrithione to 8-hydroxyquinoline or a salt thereof of from 1:5 to 5:1, or the at least one antimicrobial agent comprising a zinc pyrithione and N,N-bis(2-hydroxybenzyl)ethylenediamine-N,N-diacetic acid or a salt thereof are present in a weight ratio of the at least one antimicrobial agent comprising a zinc pyrithione to N,N-bis(2-hydroxybenzyl ethylenediamine-N,N-diacetic acid or a salt of from 1:100 to 1:10.

8. The method of claim 7, wherein the iron-chelator comprises a sodium, potassium, calcium, magnesium, or copper salt of 2-hydroxypyridine-1-oxide.

9. The method of claim 8, wherein the iron-chelator comprises a zinc salt of 2-hydroxypyridine-1-oxide.

10. The method of claim 7, wherein the composition is present in water and the at least one antimicrobial agent is present in an amount of from about 10 ppm to about 1000 ppm and wherein the chelator is present in an amount of from about 100 ppm to about 500 ppm, based on the weight of the water.

11. The method of claim 7, wherein the composition is present in water and the at least one antimicrobial agent is present in an amount of from about 50 ppm to about 1000 ppm and wherein the chelator is present in an amount of from about 100 ppm to about 500 ppm, based on the weight of the water.

12. The antimicrobial composition of claim 1, wherein the iron-chelator comprises 8-hydroxyquinoline or a salt thereof.

13. The antimicrobial composition of claim 1, wherein the iron-chelator comprises a zinc salt of 8-hydroxyquinoline.

14. The antimicrobial composition of claim 1, wherein the iron-chelator comprises a salt of N,N-bis(2-hydroxybenzyl)ethylenediamine-N,N-diacetic acid or a salt thereof.

15. The antimicrobial composition of claim 1, wherein the iron-chelator comprises a zinc salt of N,N-bis(2-hydroxybenzyl)ethylenediamine-N,N-diacetic acid.

16. The method of claim 7, wherein the iron-chelator comprises 8-hydroxyquinoline or a salt thereof.

17. The method of claim 7, wherein the iron-chelator comprises a zinc salt of 8-hydroxyquinoline.

18. The method of claim 7, wherein the iron-chelator comprises a salt of N,N-bis(2-hydroxybenzyl)ethylenediamine-N,N-diacetic acid or a salt thereof.

19. The method of claim 7, wherein the iron-chelator comprises a zinc salt of N,N-bis(2-hydroxybenzyl)ethylenediamine-N,N-diacetic acid.

* * * * *